United States Patent
Prevost et al.

(10) Patent No.: US 6,846,822 B2
(45) Date of Patent: Jan. 25, 2005

(54) PRODUCT COMPRISING A HETEROTRIMERIC G PROTEIN SIGNAL TRANSDUCTION INHIBITOR ASSOCIATED WITH ANTI-HYPERTENSIVE AGENT FOR THERAPEUTIC USE IN THE TREATMENT OF ARTERIAL HYPERTENSION

(75) Inventors: Grégoire Prevost, Antony (FR); Marc Teillot, Paris (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 10/169,656

(22) PCT Filed: Jan. 5, 2001

(86) PCT No.: PCT/FR01/00027

§ 371 (c)(1),
(2), (4) Date: Jul. 3, 2002

(87) PCT Pub. No.: WO01/49322

PCT Pub. Date: Jul. 12, 2001

(65) Prior Publication Data

US 2003/0004168 A1 Jan. 2, 2003

(30) Foreign Application Priority Data

Jan. 6, 2000 (FR) .............................. 00 00105

(51) Int. Cl.$^7$ .......................................... A61K 31/4985
(52) U.S. Cl. ...................................... 514/249; 544/350
(58) Field of Search .......................... 514/249; 544/350

(56) References Cited

FOREIGN PATENT DOCUMENTS

WO          9730053          8/1997

*Primary Examiner*—Richard L. Raymond
(74) *Attorney, Agent, or Firm*—Muserlian, Lucas and Mercanti

(57) ABSTRACT

The invention concerns a product comprising at least an inhibitor of heterotrimeric G protein signal transduction, associated with at least another anti-hypertensive agent, in particular calcium channel blockers and conversion enzyme inhibitors, for simultaneous, separate or prolonged therapeutic use, in the treatment of hypertension.

20 Claims, 3 Drawing Sheets

Figure 1:
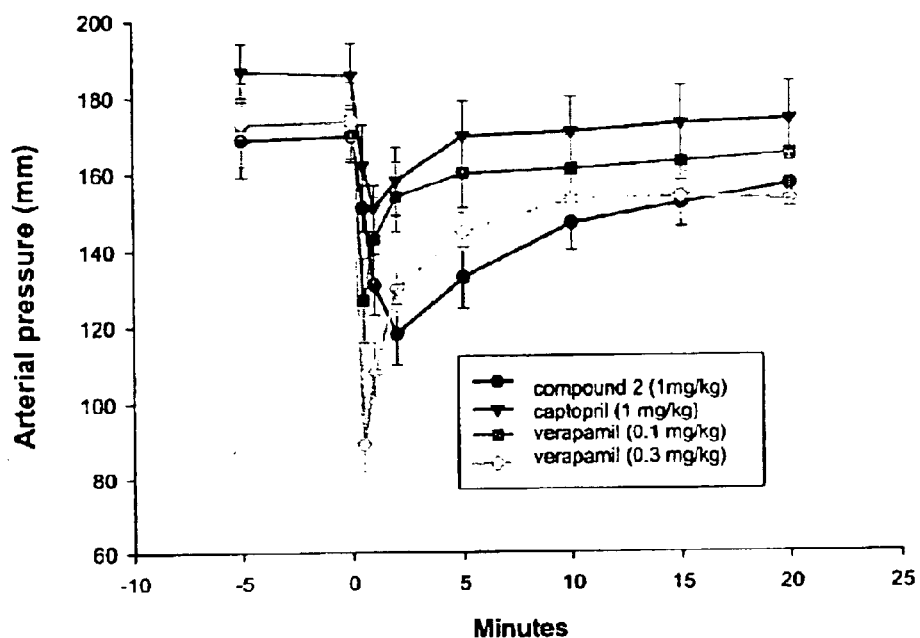

PRODUCT COMPRISING A HETEROTRIMERIC G PROTEIN SIGNAL TRANSDUCTION INHIBITOR ASSOCIATED WITH ANTI-HYPERTENSIVE AGENT FOR THERAPEUTIC USE IN THE TREATMENT OF ARTERIAL HYPERTENSION

This application is a 371 of PCT/FR01/00027 filed Jan. 5, 2001.

The present invention relates to a product comprising at least one G protein inhibitor, and preferably a compound of general formula (I) defined below, combined with at least one anti-hypertensive agent, preferably chosen from the group comprising calcium channel antagonists or conversion enzyme inhibitors, for simultaneous, separate or spread over time therapeutic use, in the treatment of arterial hypertension.

Arterial hypertension is a very common disease and one to which a high morbidity and mortality rate is associated. According to age, treatment of hypertension must be considered when the systolic arterial pressure is higher than 160–180 mm of mercury and the diastolic pressure higher than 100–110 mm of mercury.

The optimum strategy for the care of patients suffereing from hypertension is still under discussion. Non-pharmacological treatment (reduction of sodium intake in food, loss of weight, physical exercise, giving up tobacco products etc.) is a possibility in patients with moderate hypertension. Pharmacological treatment begins with monotherapy, which allows satisfactory blood pressure control in 50–60% of patients. Changing therapeutic class as well as combination with another class of anti-hypertensive agents represent the alternative treatments in the event of resistance to the first therapy (Beaufils and Clement, *Drugs*, 56, 11–21, (1998)).

Anti-hypertensive medicaments can be divided into several classes:

thiazidic and similar diuretics such as hydrochlorothiazide, cicletanine, xipamide, indapamide and clopamide;

loop diuretics such as furosemide, piretanide and bumetanide;

hyperkalaemia causing (potassium-sparing) diuretics such as amiloride, spironolactone and canrenone;

beta-blockers such as propranolol, acebutolol, atenolol, nadolol, bisoprolol, metoprolol, pindolol, oxprenolol and betaxolol;

conversion enzyme inhibitors (CEI) such as captopril, enalapril, benazepril, lisinopril, quinapril, ramipril and imidapril;

Angiotensin II receptor antagonists (ARBs), such as losartan, candesartan, cilexetil, irbesartan, telmisartan, and valsartan;

Slow calcium channel antagonists, such as nifedipine, amlodipine, felodipine, isradipine, diltiazem, bepridil, lacidipine, nitrendipine, nicardipine and verapamil;

central anti-hypertensive agents such as clonidine, guanfacine, monoxidine, rilmenidine and α-methyl-dopa;

alpha-blockers such as prasozine, urapidil, doxazosine and terazosine;

vasodilators such as hydralazine, dihydralazine and minoxidil.

Furthermore, the development of new anti-hypertensive treatments of course involves the discovery of new molecules (cf. Singh et al, *Drugs*, 58(4):579–87 (October 1999); (Mancia et al, *Curr. Opin. Cardiol.*, 14(5):375–80 (September 1999); Cases, *Drug new Perspect.*, 12(6) 372–377 (1999)). Among the new families of molecules intended for the treatment of hypertension, the following can in particular be mentioned:

vasopeptidase inhibitors; and endothelin antagonists.

More recently, allelic variations of the genes coding for the angiotensinogen, the β2-adrenergic receptor, and the β3 sub-unit of the G protein have been identified. (Luft, F. C., *Journal of hypertension*, 16, 1871–1878, (1998)). In addition, the results of Anand-Srivastava (*Mol. Cell. Biochem.*, 175, 163–170, (1996)) suggest that the increase in the expression of the Gi α-2 and Gi α-3 proteins in the heart and the aorta which precedes the development of an increase in arterial pressure in the SHR rat (Spontaneously Hypertensive Rat) can be one of the factors causing hypertension. Similarly, the βγ sub-units of the G protein seem to be involved in the control of the recurrence of stenosis and the proliferation of smooth vascular muscle cells (Iaccarino et al., *Proc. Nat. Acad. Sci. USA*, 96, 3945–3950,(1999)). Blocking of these sub-units by a βARKct peptide prevents proliferation. On the other hand, a Gi protein inhibitor, pertussic toxin, is capable of lowering the arterial pressure of the SHR rat by intravenous injection. This lowering of pressure is observed for two weeks and seems more marked in the hypertensive rat than in the normotensive rat (Kost et coll, Clinical and Experimental Pharmacology and Physiology, 26, 449–455, (1999)). Similarly the renal vascular tonus in the SHR rat is modified by pertussic toxin with an increase in renal vascular flux and a reduction in renal vascular resistance.

Together, these recent works suggest that heterotrimeric G protein can represent a therapeutic target for the control of hypertension by the development of products specifically targeting this transduction signal. The G protein participates in the transmission of signals from outside the cell towards the interior thanks to its interaction with the receptors with seven transmembrane fields using different effectors including adenylate cyclase, C phospholipase or also ionic canals (cf. Gilman, A. G., *Biosci. Rep.*, 15, 65–97 (1995)).

The Applicant has furthermore described specific inhibitors of signal transduction by heterotrimeric G proteins in the PCT patent application WO 00/02558 (which describes the use of the compounds of General Formula (I) hereafter, already known as farnesyltransferase inhibitors (cf. WO 97/30053), as inhibitors of the transduction of heterotrimeric G protein signals) and WO 00/02881.

When the limit of the efficacy of monotherapy is reached, the discovery of effective combinations of different therapeutic classes is sought to combine the effect of each class and better combat hypertension of multifactorial origin. For example, a combination using beta-blockers and calcic antagonists is effective in 80 to 85% of cases. This combination allows doses to be reduced in comparison to the doses used in monotherapy.

The Applicant shows in the present Application that the combination of a G protein inhibitor with another anti-hypertensive agent, preferably an anti-hypertensive agent from another class, allows hypertension to be reduced more effectively. A product according to the invention offers the advantage of allowing lower doses of the anti-hypertensive agents chosen to be used, which has the main effect of reducing the side effects of the treatment whilst obtaining an equivalent therapeutic benefit.

A subject of the invention is therefore a product comprising at least one inhibitor of the transduction of heterotrimeric G protein signals combined with at least one anti-hypertensive agent, preferably an anti-hypertensive agent from another class, said anti-hypertensive agent being preferably chosen from the group comprising calcium channel inhibitors and conversion enzyme inhibitors for simultaneous, separate or spread over time therapeutic use, in the treatment of arterial hypertension.

Preferably, a product according to the invention will comprise a heterotrimeric G protein signal transduction inhibitor corresponding to general formula (I)

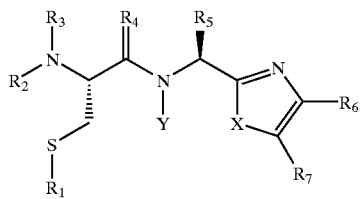

(I)

corresponding to sub-formulae ($I_A$) or ($I_B$):

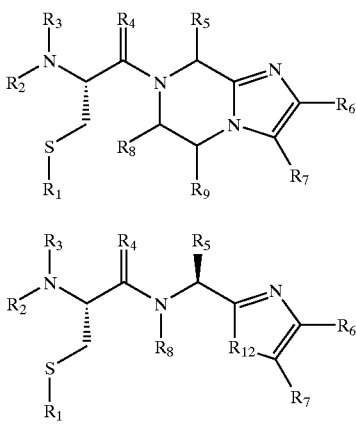

in which:
X represents $R_{12}$ and Y represents $R_8$, or X and Y complete a ring with 6 members, X-Y together representing the —CH($R_8$)—CH($R_9$)— radical;
$R_1$ represents H, an alkyl or lower alkylthio radical;
$R_2$ and $R_3$ independently represent H or a lower alkyl radical;
$R_4$ represents $H_2$ or O;
$R_5$ represents H, or one of the lower alkyl, lower alkenyl, lower alkynyl, cycloalkyl, cycloalkylalkyl, aryl, lower arylalkyl, heterocycle or lower alkyl heterocycle radicals, these radicals being optionally substituted by radicals chosen from the group comprising a lower alkyl radical, —O—$R_{10}$, —S(O)$_m R_{10}$ (m representing 0, 1, or 2), —N($R_{10}$)($R_{11}$), —N—C(O)—$R_{10}$, —NH—(SO$_2$)—$R_{10}$, —CO$_2$—$R_{10}$, C(O)—N($R_{10}$)($R_{11}$) and —(SO$_2$)—N($R_{10}$)($R_{11}$);
$R_6$ and $R_7$ independently represent H, a —C(O)—NH—CHR$_{13}$—CO$_2$R$_{14}$ radical, or one of the lower alkyl, aryl, lower arylalkyl, lower arylsulphonylalkyl, lower aralkoxyalkyl, heterocycle or lower alkyl heterocycle radicals, these radicals being optionally substituted by radicals chosen from the group comprising OH, alkyl or lower alkoxy, N($R_{10}$)($R_{11}$), COOH, CON($R_{10}$)($R_{11}$), and halo radicals, or $R_6$ and $R_7$ together form an aryl radical or a heterocycle;
$R_8$ and $R_9$ independently represent, H or one of the lower alkyl, aryl, lower arylalkyl, heterocycle or lower alkyl heterocycle radicals, these radicals being optionally substituted by radicals chosen from the group comprising the OH, alkyl or lower alkoxy, N($R_{10}$)($R_{11}$), COOH, CON($R_{10}$)($R_{11}$) and halo radicals, or $R_8$ and $R_9$ together form an aryl radical or a heterocycle;
$R_{10}$ and $R_{11}$, independently represent H, an aryl radical or heterocycle, or an alkyl, arylalkyl or lower alkyl heterocycle radical;
$R_{12}$ represents NR$_9$, S, or O;
$R_{13}$ represents a lower alkyl radical optionally substituted by a radical chosen from the lower alkyl, —OR$_{10}$, —S(O)$_m$R$_{10}$ (m representing 0, 1, or 2) and —N(R$_{10}$)(R$_{11}$) radicals;
$R_{14}$ represents H or a lower alkyl radical;
the compound of general formula (I) can if appropriate also be presented in the dimer form of a disulphide;
or a pharmaceutically acceptable salt of a compound of general formula (I) or if appropriate of its dimer.

By lower alkyl radical, is meant a linear or branched alkyl radical containing 1 to 6 carbon atoms, and in particular the methyl, ethyl, propyl, isopropyl, butyl, isobutyl, sec-butyl and tert-butyl, pentyl, neopentyl, isopentyl, hexyl, isohexyl radicals. By heterocycle radical, is meant a radical constituted by one or more rings and including at least one heteroatom (O, N or S). By aryl radical, is meant a carbocyclic mono- or polycyclic aromatic system comprising at least one aromatic ring (and, in particular, the phenyl radical which can be abbreviated to Ph). By arylalkyl, alkyl heterocycle, alkylthio or lower alkoxy radical, is meant the radicals in which the alkyl radical has the meaning as indicated previously.

Preferably, the compounds of general formula (I) are such that:
X and Y complete a ring with 6 members, X—Y together representing the —CH($R_8$)—CH($R_9$)— radical;
$R_1$ represents an alkyl or lower radical;
$R_2$ and $R_3$ represent H;
$R_4$ represents O;
$R_5$ represents H, or one of the lower alkyl, cycloalkyl, cycloalkylalkyl, lower arylsulphonylalkyl, lower aralkoxyalkyl radicals, these radicals being optionally substituted by radicals chosen from the group comprising a lower alkyl or —O—$R_{10}$ radical;
$R_6$ and $R_7$ represent independently H or an aryl radical optionally substituted by radicals chosen from the group comprising the OH, alkyl or lower alkoxy radicals,
$R_8$ and $R_9$ represent H;
and $R_{10}$ and $R_{11}$, represent independently H or a lower alkyl radical.

The following compounds of General Formula (I) are in particular preferred for the invention:

7-(2-amino-1-oxo-3-thiopropyl)-8-(cyclohexylmethyl)-2-(2-methylphenyl)-5,6,7,8-tetrahydroimidazo[1,2a] pyrazine;
7-(2-amino-1-oxo-3-thiopropyl)-8-butyl-2-(2-methoxyphenyl) -5,6,7,8-tetrahydroimidazo[1,2a] pyrazine;
bis-1,1'-[7-(2-amino-1-oxo-3-thiopropyl)-2-(2-methoxyphenyl)-8-(1-methylpropyl)-5,6,7,8-tetrahydroimidazo[1,2a]pyrazine] disulphide;
bis-1,1'-[7-(2-amino-1-oxo-3-thiopropyl)-8-(cyclohexylmethyl)-2-(2-methoxyphenyl)-5,6,7,8-tetrahydroimidazo[1,2a]pyrazine disulphide;
bis-1,1'-7-(2-amino-1-oxo-3-thiopropyl-(2-(1-naphthyl)-8-(2-methylpropyl)-5,6,7,8-tetrahydroimidazo[1,2a] pyrazin-7-yl) disulphide;

7-(2-amino-1-oxo-3-thiopropyl)-8-(cyclohexylmethyl)-2-phenyl-5,6,7,8-tetrahydroimidazo[1,2a]pyrazine;

7-(2-amino-1-oxo-3-thiopropyl)-2-(2-methoxyphenyl)-8-(phenylmethoxy)methyl-5,6,7,8-tetrahydroimidazo[1,2a]pyrazine;

7-(2-amino-1-oxo-3-thiopropyl)-2-(2-methoxyphenyl) -8-(1-phenylmethoxy)ethyl-5,6,7,8-tetrahydroimidazo[1,2a]pyrazine;

7-(2-amino-1-oxo-3-thiopropyl)-2-(2-methoxyphenyl)-8-(phenoxyethyl)-5,6,7,8-tetrahydroimidazo[1,2a]pyrazine;

7-(2-amino-1-oxo-3-thiopropyl)-2-(2-methoxyphenyl)-8-(phenoxyethyl)-5,6,7,8-tetrahydro-imidazo[1,2a]pyrazine, or its dimeric form;

and 7-(2-amino-1-oxo-3-thiopropyl)-2-(2-methoxyphenyl)-8-(phenylsulphonylethyl)-5,6,7,8-tetrahydro-imidazo[1,2a]pyrazine;

or a pharmaceutically acceptable salt of one of the latter

As far as the anti-hypertensive agent combined with the heterotrimeric G protein signal transduction inhibitor is concerned, although the calcium channel inhibitors and the conversion enzyme inhibitors, and in particular verapamil and captopril, are preferred, a number of other anti-hypertensive agents can also be used according to the invention, such as thiazidic diuretics and substitutes, loop diuretics, potassium-sparing diuretics, antialdosterones, beta-blockers, angiotensin receptor antagonists, anti-hypertensive agents, alpha-blockers and vasodilatatory agents, vasopeptidase inhibitors and endothelin antagonists.

According to a particularly preferred variant of the invention, the heterotrimeric G protein signal transduction inhibitor used in the composition of a product according to the invention is chosen from the following compounds:

7-(2-amino-1-oxo-3-thiopropyl)-8-(cyclohexylmethyl)-2-phenyl-5,6,7,8-tetrahydroimidazo[1,2a]pyrazine; and 7-(2-amino-1-oxo-3-thiopropyl)-8-(cyclohexylmethyl)-2-(2-methylphenyl)-5,6,7,8-tetrahydroimidazo[1,2a]pyrazine;

and pharmaceutically acceptable salts of the latter.

Still according to a particularly preferred variant of the invention, anti-hypertensive agents combined with said inhibitors of the transduction of heterotrimeric G protein signals are chosen from the group composed of:

calcium channel antagonists, and in particular verapamil;

conversion enzyme inhibitors, and in particular captopril;

and pharmaceutically acceptable salts of the latter.

Optionally, a second anti-hypertensive agent, different from the heterotrimeric G protein signal transduction inhibitor and the anti-hypertensive agent which is already combined with it, can be combined with a product according to the invention. Said anti-hypertensive agent can be chosen from those already mentioned in the present application. The following products are particularly preferred, combining:

a heterotrimeric G protein signal transduction inhibitor, a loop diuretic and hyperkalaemia causing diuretic;

a heterotrimeric G protein signal transduction inhibitor, a thiazidic or related diuretic and a hyperkalaemia causing diuretic;

a heterotrimeric G protein signal transduction inhibitor, a conversion enzyme inhibitor and a thiazidic diuretic;

a heterotrimeric G protein signal transduction inhibitor, an angiotensin II receptor antagonist and a thiazidic diuretic;

a heterotrimeric G protein signal transduction inhibitor, a beta-blocker and a diuretic;

a heterotrimeric G protein signal transduction inhibitor, a beta-blocker and a calcium channel antagonist;

a heterotrimeric G protein signal transduction inhibitor, a beta-blocker and a vasodilatory agent.

A subject of the invention is also a pharmaceutical composition comprising a product according to the invention, with optionally one or more pharmaceutically acceptable excipients.

The pharmaceutical compositions comprising a compound of the invention can be in the form of solids, for example powders, granules, tablets, gelatin capsules, liposomes or suppositories. The appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions comprising a compound of the invention can also be presented in liquid form, for example solutions, emulsions, suspensions or syrups. The appropriate liquid supports can be, for example, water, organic solvents such as glycerol or glycols, and similarly their mixtures in varying proportions in water.

The administration of a medicament according to the invention can be done by topical, oral, parenteral route, by injection (intramuscular, sub-cutaneous, intravenous, etc.), etc. The administration route will of course depend on the type of disease to be treated.

The dose of a product according to the present invention, to be provided for the treatment of the diseases or afflictions mentioned above, varies according to the method of administration, the age and the body weight of the subject to be treated as well as the condition of the latter, and will be decided definitively by the attending doctor or vet. Such a quantity determined by the attending doctor or vet is referred to here as "therapeutically effective amount".

The following administration doses (daily, except where otherwise indicated) can in particular be envisaged for the different compounds used in the composition of a product according to the invention:

compound of General Formula (I): 0.1 to 100 mg/kg by intravenous route; and 50 to 1000 mg orally per day in several doses verapamil: 50 to 500 mg orally per day in several doses;

captopril: 50 to 500 mg orally per day in several doses.

For the other compounds used in the composition of the products according to the invention, the daily administration doses are fixed by the attending doctor or vet within the limit of doses of these compounds usually administered for the treatment of arterial hypertension, which can in particular be found in a reference work (such as, for example, the *Dictionnaire VIDAL®*, the *Rote Liste®* or the *Physician's Desk Reference®*).

Unless they are defined in another manner, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented to illustrate the above procedures and should in no way be considered as limiting the scope of the invention.

Preparation of the Compounds of General Formula (I) Used in the Composition of the Products of the Invention A) The compounds of General Formula (I) can be prepared according to methods similar to those described in PCT patent application WO 97/30053.

B) The preparation of certain specific compounds of General Formula (I), not described in PCT Application WO 97/30053, is described in PCT Application WO 00/02881.

EXAMPLES

In order to illustrate the usefulness of the invention, the effect on the arterial pressure of spontaneously hypertensive type rats of treatment with 7-(2-amino-1-oxo-3-thiopropyl)-8-(cyclohexylmethyl)-2-phenyl-5,6,7,8-tetrahydroimidazo [1,2a]pyrazine (hereafter designated compound 2, described in Application WO 00/02881), combined with anti-hypertensive agents of two different classes, namely conversion enzyme inhibitors (captopril) and calcium channel inhibitors (verapamil) will be studied.

1) Procedures

13/14 week old male SHR rats (Charles River France) are anaesthetized using pentobarbital (Sanofi) (60 mg/kg/IP). A carotid artery is catheterised for measuring arterial pressure and heart rate (Gould pressure and physiography sensors, Buxco acquisition software version 1.5.7 and Analyst analysis software version 1.35 (EMKA)). A jugular vein is catheterised for the injection of the anti-hypertensive agent, compound 2 is injected into the vein of the penis. After a stabilization period of 10 minutes, the product or two products simultaneously are administered and their effects are monitored for 20 minutes.

For administration purposes, 7-(2-amino-1-oxo-3-thiopropyl)-8-(cyclohexylmethyl)-2-phenyl-5,6,7,8-tetrahydro-imidazo[1,2a]pyrazine, verapamil (Sigma, USA) and captopril (Sigma, USA) can be dissolved in an aqueous solution of NaCl at 0.9%.

The following groups (of 4 to 6 animals) are formed by:
compound 2 (1 mg/kg);
captopril (1 mg/kg);
verapamil (0.1 and 0.3 mg/kg);
captopril (1 mg/kg)+compound 2 (1 mg/kg);
verapamil (0.1 or 0.3 mg/kg)+compound 2 (1 mg/kg);

2) Results

The anaesthetized spontaneously hypertensive rats present an average arterial pressure varying between 165–190 mm. (cf. FIGS. 1, 2 and 3).

Treatments by a single intravenous injection of the calcium channel inhibitor verapamil (0.1 mg/kg or 0.3 mg/kg), or the conversion enzyme inhibitor captopril (1 mg/kg) or the heterotrimeric G protein inhibitor (1 mg/kg) lead to an immediate reduction (less than 2 minutes) in arterial pressure with a return to initial values 20 minutes after the injections are carried out at time 0 (FIG. 1).

Figure 2:
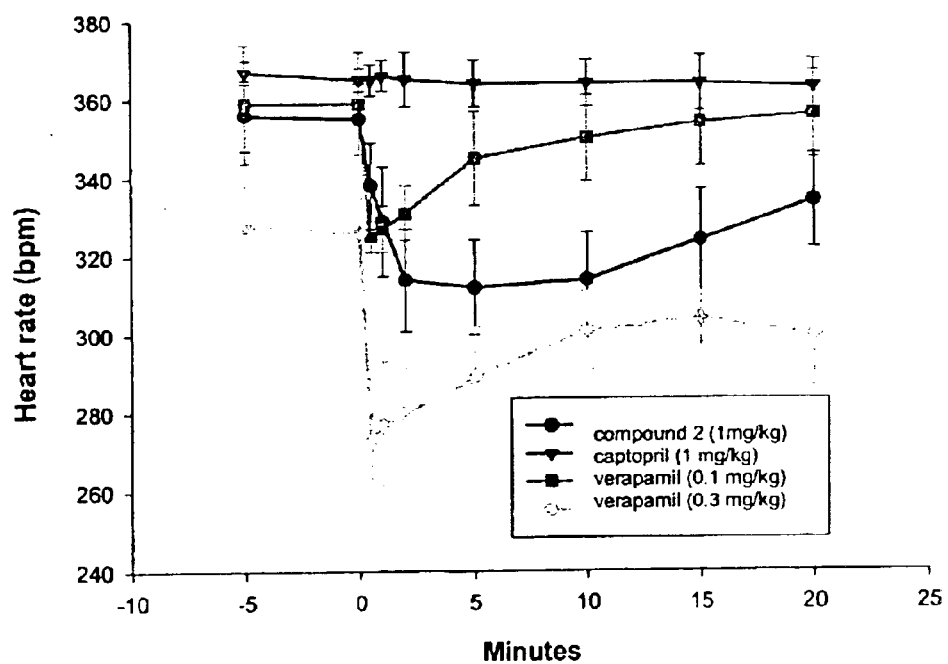

Furthermore, the heart rates measured in these SHR rats, anaesthetized before injection, are between 328 and 371 beats per minute. The heart rates measured in these SHR rats treated with the same products, shown in FIG. 2, are changed very little by these different treatments. Captopril does not change the heart rate at all, whilst verapamil (0.1 and 0.3 mg/kg) or the G protein inhibitor (1 mg/kg) induce a reduction with a maximum difference (delta) of 32, 56 and 44 respectively.

The combination of several anti-hypertensive agents is frequently prescribed in order to obtain a stabilization of arterial pressure.

The combination of a G protein inhibitor and two other therapeutic classes is illustrated below.

Figure 3:
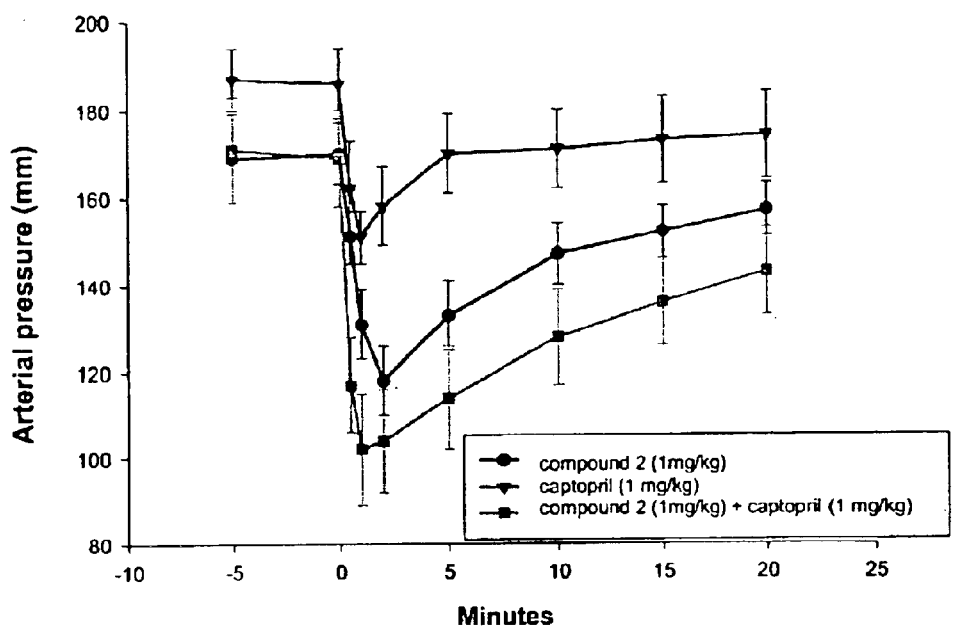

FIG. 3 shows that the "G protein inhibitor+captopril" combination induces a reduction in arterial pressure in the SHR rat higher than the activity of the two products alone.

Figure 4:
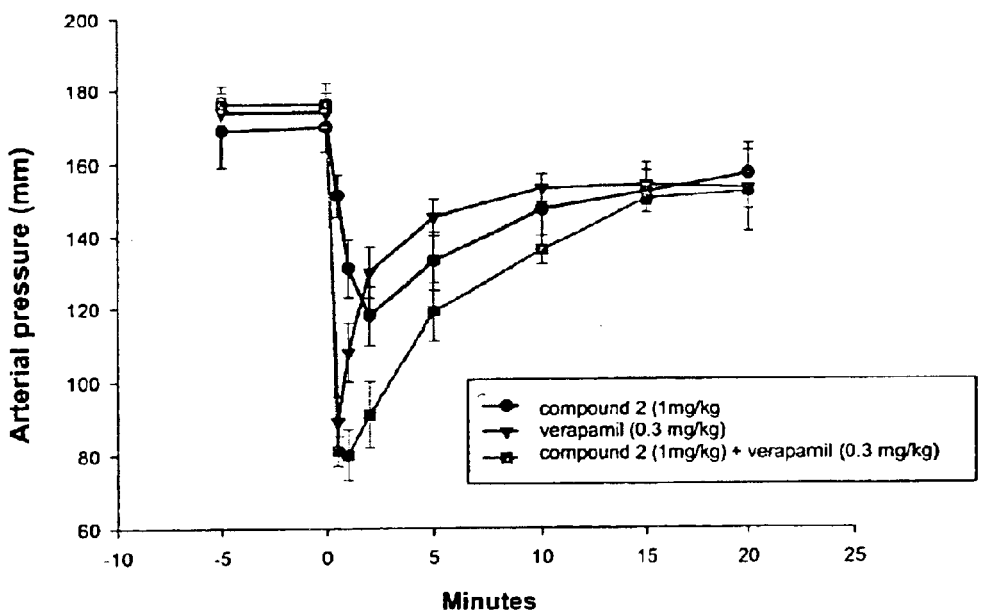

On the other hand, FIG. 4 shows that the G protein inhibitor+captopril combination does not induce a reduction in the heart rate in the SHR rat higher than the activity of the two products alone.

Figure 5:
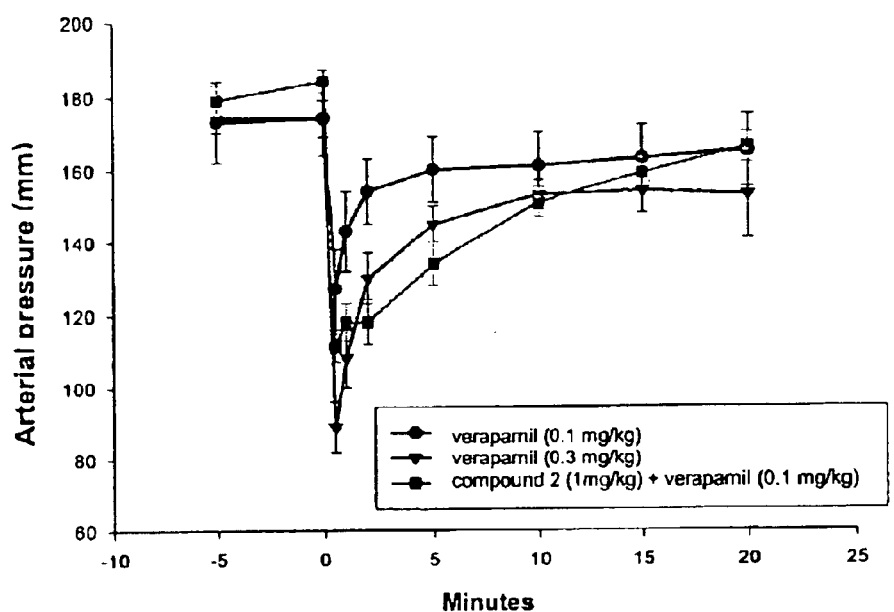

FIG. 5 shows that the "G protein inhibitor+verapamil" combination induces a reduction in arterial pressure in the SHR rat higher than the activity of the two products alone. The "G protein inhibitor+verapamil combination at a dose of 0.1 mg/kg" gives a profile similar to the action of verapamil alone, but at a dose which is 3 times greater i.e. 0.3 mg/kg (FIG. 5).

Figure 6:
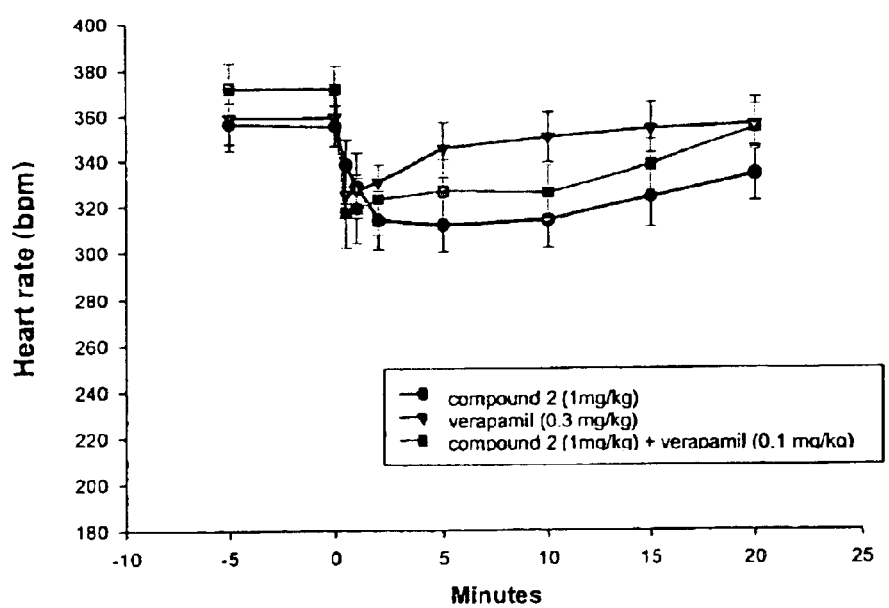

On the other hand, the results illustrated by FIG. 6 and the table below show that the "G protein inhibitor+verapamil" combination does not induce a reduction in the heart rate in the SHR rat higher than the activity of the two products alone.

| Product | Dose(s) (mg/kg) | Frequency difference (Δ) |
|---|---|---|
| Compound 2 | 1 | 44 |
| Captopril | 1 | 1 |
| Verapamil | 0.1 | 28 |
| Verapamil | 0.3 | 56 |
| Compound 2 + captopril | 1 and 1 | 25 |
| Compound 2 + verapamil | 1 and 0.1 | 54 |
| Compound 2 + verapamil | 1 and 0.3 | 52 |

What is claimed is:

1. A composition comprising a compound of the formula

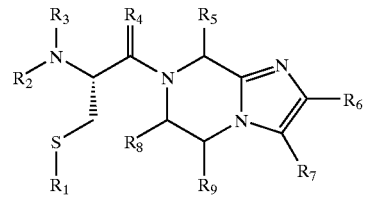

(I$_A$)

wherein R$_1$ is selected from the group consisting of H, alkyl and alkylthio of 1 to 6 carbon atoms;

R$_2$ and R$_3$ are independently H or alkyl;

R$_4$ is H$_2$ or O,

R$_5$ is selected from the group consisting of H, alkyl of 1 to 6 carbon atoms, alkenyl of up to 6 carbon atoms, cycloakyl, cycloalkylalkyl with alkyl of 1 to 6 carbon atoms, aryl and arylalkyl with alkyl of 1 to 6 carbon atoms, these groups are unsubstituted or substituted with a member selected from the group consisting of alkyl of 1 to 6 carbon atoms, —O—R$_{10}$, —S(O)$_m$R$_{10}$, m is 0, 1 or 2, —N(R$_{10}$)(R$_{11}$), —N—C(O)—R$_{10}$, —CO$_2$—R$_{10}$, C(O)—N(R$_{10}$)R$_{11}$), and —(SO$_2$)—N(R$_{10}$)(R$_{11}$);

R$_6$ and R$_7$ are independently selected from the group consisting of H, —C(O)—NH—CHR$_1$—CO$_2$R$_{14}$, alkyl of 1 to 6 carbon atoms, aryl and arylalkyl with alkyl of 1 to 6 carbon atoms, these groups being unsubstituted or substituted with a member selected from the group consisting of OH, alkyl and akoxy of 1 to 6 carbon atoms, —N(R$_{10}$)(R$_{11}$), —COOH, —CON(R$_{10}$)(R$_{11}$), and halo, or R$_6$ and R$_7$ together form aryl or heterocycle;

R$_8$ and R$_9$ are independently selected from the group consisting of H or 11 to 6 carbon atoms, aryl and arylalkyl with alkyl of 1 to 6 carbon atoms, these groups are unsubstituted or substituted by a member selected from the group consisting of OH, alkyl and alkoxy of 1 to 6 carbon atoms, —N($R_{10}$)($R_{11}$), —CON($R_{10}$)($R_{11}$) and halo, or $R_8$ and $R_9$ form together aryl; $R_{10}$ and $R_{11}$ are independently selected from the group consisting of H, aryl, alkyl of 1 to 6 carbon atoms, arylalkyl;

$R_{12}$ is —$NR_9$—, —S—, or —O—;

$R_{13}$ is alkyl of 1 to 6 carbon atoms unsubstituted or substituted by a member selected from the group consisting of 1 to 6 carbon atoms, —$OR_{10}$, —$S(O)_m R_{10}$, m is 0, 1 or 2, and —N($R_{10}$)($R_{11}$);

$R_{14}$ is H or alkyl of 1 to 6 carbon atoms; and its pharmaceutically acceptable acid addition salt and at least one other anti-hypertensive agent for the treatment of arterial hypertension.

2. A composition of claim 1, wherein

X and Y complete a ring with 6 members, X-Y together being —CH($R_8$)—CH($R_9$)—;

$R_1$ is alkyl of 1 to 6 carbon atoms;

$R_2$ and $R_3$ are H;

$R_4$ is O;

$R_5$ is selected from the group consisting of H, alkyl of 1 to 6 carbon atoms, alkenyl of up to 6 carbon atoms, alkynyl of up to 6 carbon atoms, cycloalkyl, cycloalkylalkyl with alkyl of 1 to 6 carbon atoms, arylsulfonylalkyl with alkyl 1 of 1 to 6 carbon atoms, aralkoxyalkyl, alkoxy and alkyl of 1 to 6 carbon atoms, these groups are unsubstituted or substituted by alkyl of 1 to 6 carbon atoms or —O—$R_{10}$;

$R_6$ and $R_7$ are independently H, or aryl unsubstituted or substituted by a member selected from the group consisting of OH, alkyl and lower alkoxy of 1 to 6 carbon atoms, $R_8$ and $R_9$ are H;

and $R_{10}$ and $R_{11}$ are independently H or alkyl of 1 to 6 carbon atoms.

3. A product composition of claim 1 wherein the compound of formula ($1_A$) is selected from the group consisting of 7-(2-amino-1-oxo-3-thiopropyl)-8-(cyclohexylmethyl)-2-(2-methylphenyl)-5,6,7,8-tetrahydroimidazo[1,2a]pyrazine;

7-(2-amino-1-oxo-3-thiopropyl)-8-butyl-2-(2-methyoxyphenyl)-5,6,7,8-tetrahydroimidazo[1,2a]pyrazine;

bis-1,1'-[7-(2-amino-1-oxo-3-thiopropyl)-2-(2-methoxyphenyl)-8-(1-methylpropyl)-5,6,7,8-tetrahydroimidazo[1,2a]pyrazine]disulfide;

bis-1,1'-[7-(2-amino-1-oxo-3-thiopropyl)-8-(cyclohexylmethyl)-2-(2-methoxyphenyl)-5,6,7,8-tetrahydroimidazo[1,2a]pyrazinedisulfide;

bis-1,1'-7-(2-amino-1-oxo-3-thiopropyl-(2-(1-naphthyl)-8-(2-methylpropyl)5,6,7,8-tetrahydroimidazo[1,2a]pyrazin-7-yl)disulfide;

7-(2-amino-1-oxo-3-thiopropyl)-8-(cyclohexylmethyl)-2-phenyl-5,6,7,8-tetrahydroimidazo[1,2a]pyrazine;

7-(2-amino-1-oxo-3-thiopropyl)-2-(2-methoxyphenyl)-8-(phenylmethoxy)methyl-5,6,7,8-tetrahydroimidazo[1,2a]pyrazine;

7-(2-amino-1-oxo-3-thiopropyl)-2-(2-methoxyphenyl)-8-(1-phenylmethoxy)ethyl-5,6,7,8-tetrahydroimidazo[1,2a]pyrazine;

7-(2-amino-1-oxo-3-thiopropyl)-2-(2-methoxyphenyl)-8-(phenoxyethyl)5,6,7,8-tetrahydroimidazo[1,2a]pyrazine;

7-(2-amino-1-oxo-3-thiopropyl)-2-(2-methoxyphenyl)-8-(phenoxyethyl)5,6,7,8-tetraydro-imidazo[1,2a]pyrazine, or its form dimeric;

and 7-(2-amino-1-oxo-3-thiopropyl)-2-(2-methoxyphenyl)-8-phenylsulfonylethyl)-5,6,7,8-tetrahydro-imidazo[1,2a]pyrazine; and its pharmaceutically acceptable acid addition salt.

4. A composition of claim 2, wherein the compound of formula ($I_A$) is 7-(2-amino-1-oxo-3-thiopropyl)-8-cyclohexylmethyl)-2-phenyl-5,6,7,8-tetrahydro-imidazo[1,2]pyrazine or its pharmaceutically acceptable acid addition salt.

5. A composition of claim 1 wherein the second anti-hypertensive agent combined with the compound of the formula IA is selected from the group consisting of calcium channel inhibitors, conversion enzyme inhibitors, thiazidic diuretics, loop diuretics, potassium-sparing diuretics, antialdosterones, beta-blockers, angiotensin receptor antagonists, anti-hypertensive agents, alpha-blockers, vasodilatory agents, vasopeptidase inhibitors and endothelin antagonists.

6. A composition of claim 5 wherein the second anti-hypertensive agent is a calcium channel inhibitor.

7. A composition of claim 6, wherein the second anti-hypertensive agent is verapamil.

8. A composition of claim 5, wherein the second anti-hypertensive agent is a conversion enzyme inhibitor.

9. A composition of claim 8, wherein the second anti-hypertensive agent is captopril.

10. A composition of claim 1, wherein the second anti-hypertensive agent, different from the compound of formula IA are already combined with it.

11. A composition of claim 10 wherein the second anti-hypertensive agent is a loop diuretic and is combined with a hyperkalaemia causing diuretic.

12. A composition of claim 10, wherein the second anti-hypertensive agent is a thiazidic or related diuretic and is combined with a hyperkalaemia causing diuretic.

13. A composition of claim 10, wherein the second anti-hypertensive agent is a conversion enzyme inhibitor and is combined with a thiazidic diuretic.

14. A composition of claim 10, wherein the second anti-hypertensive agent is an antagonist of angiotensin II receptors and is combined with a thiazidic diuretic.

15. A composition of claim 10, wherein the second anti-hypertensive agent is a beta-blocker and is combined with a diuretic.

16. A composition of claim 10, wherein the second anti-hypertensive agent is a beta-blocker and is combined with a calcium channel antagonist.

17. A composition of claim 10, wherein the second anti-hypertensive agent is a beta-blocker and is combined with a vasodilatory agent.

18. A pharmaceutical composition for treating arterial hypertension comprising an amount of a composition of claim 1 sufficient to treat arterial hypertension and a pharmaceutically acceptable excipient.

19. A method of treating arterial hypertension in warm-blooded animals comprising administering to warm-blooded animals in need thereof an amount of a composition of claim 1 sufficient to treat arterial hypertension.

20. A method of treating arterial hypertension in warm-blooded animals comprising administering to warm-blooded animals in need thereof an amount of a composition of claim 10 sufficient to treat arterial hypertension.

* * * * *